US010339676B2

(12) United States Patent
Gajos et al.

(10) Patent No.: US 10,339,676 B2
(45) Date of Patent: Jul. 2, 2019

(54) METHOD FOR RECONSTRUCTING MULTI-TRACER METABOLIC AND MORPHOMETRIC IMAGES AND TOMOGRAPHY SYSTEM FOR MULTI-TRACER METABOLIC AND MORPHOMETRIC IMAGING

(71) Applicant: UNIWERSYTET JAGIELLONSKI, Cracow (PL)

(72) Inventors: Aleksander Gajos, Cracow (PL); Daria Kaminska, Rutki Kossaki (PL); Pawel Moskal, Czulowek (PL); Eryk Czerwinski, Cracow (PL)

(73) Assignee: UNIWERSYTET JAGIELLONSKI, Cracow (PL)

( * ) Notice: Subject to any disclaimer, the term of this patent is extended or adjusted under 35 U.S.C. 154(b) by 0 days.

(21) Appl. No.: 15/753,316

(22) PCT Filed: Sep. 7, 2015

(86) PCT No.: PCT/PL2015/050038
§ 371 (c)(1),
(2) Date: Feb. 18, 2018

(87) PCT Pub. No.: WO2017/043985
PCT Pub. Date: Mar. 16, 2017

(65) Prior Publication Data
US 2018/0247432 A1  Aug. 30, 2018

(51) Int. Cl.
*G06T 11/00* (2006.01)
*A61B 6/03* (2006.01)
(Continued)

(52) U.S. Cl.
CPC ............ *G06T 11/003* (2013.01); *A61B 6/037* (2013.01); *G01T 1/2985* (2013.01); *G06F 17/11* (2013.01);
(Continued)

(58) Field of Classification Search
CPC ................. G06T 11/003; G06T 11/006; G06T 2207/10104; A61B 6/037; G01T 1/2985; G06F 17/11
See application file for complete search history.

(56) References Cited

U.S. PATENT DOCUMENTS 7,057,178 B1 *  6/2006  Manjeshwar ......... G06T 11/005
250/363.04
7,304,309 B2 * 12/2007  Suhami .................. B82Y 20/00
250/370.11
(Continued)

*Primary Examiner* — Manav Seth
(74) *Attorney, Agent, or Firm* — Mark M. Friedman

(57) ABSTRACT

A method for reconstructing multi-tracer metabolic and morphometric images. The method includes the steps of: (a) receiving a plurality of events from positron annihilation centers obtained during measurements conducted by TOF-PET tomography; (b) reconstructing the time coordinates and the three-dimensional spatial coordinates for the plurality of events; (c) determining a common decay plane for gamma quanta originating from the positron-electron annihilation; (d) transforming the three-dimensional spatial coordinates for the gamma quanta to a two-dimensional frame of reference of the common decay plane; (e) determining the time coordinates and the spatial coordinates of a place of the annihilation in the common decay plane; and (f) transforming the time coordinates and the spatial coordinates of the place of the annihilation in the two-dimensional frame of reference of the common decay plane to three-dimensional spatial coordinates in a detector coordinate system.

3 Claims, 4 Drawing Sheets

(51) Int. Cl.
  *G01T 1/29* (2006.01)
  *G06F 17/11* (2006.01)
(52) U.S. Cl.
  CPC .. *G06T 11/006* (2013.01); *G06T 2207/10104* (2013.01)

(56) References Cited

U.S. PATENT DOCUMENTS

| | | | | |
|---|---|---|---|---|
| 7,917,192 B2* | 3/2011 | Dos Santos Varela | | G01T 1/1615 250/370.1 |
| 8,515,148 B2* | 8/2013 | Gagnon | | G01T 1/1648 382/131 |
| 8,604,440 B2* | 12/2013 | Frisch | | G01T 1/208 250/367 |
| 8,620,054 B2* | 12/2013 | Leroux | | G06T 11/006 382/131 |
| 8,767,908 B2* | 7/2014 | Leahy | | G01T 1/2985 250/363.04 |
| 9,472,000 B2* | 10/2016 | Dempsey | | G01R 33/4826 |
| 9,851,456 B2* | 12/2017 | Moskal | | G01T 1/2985 |
| 2004/0223173 A1* | 11/2004 | Arai | | H04N 1/6025 358/1.9 |
| 2006/0266946 A1* | 11/2006 | Defrise | | G01T 1/2985 250/363.03 |
| 2006/0266947 A1* | 11/2006 | Krieg | | G01T 1/2985 250/363.04 |
| 2008/0099686 A1* | 5/2008 | Defrise | | G01T 1/2985 250/363.04 |
| 2009/0072155 A1* | 3/2009 | Watson | | G01T 1/2985 250/363.03 |
| 2009/0124900 A1* | 5/2009 | Vandenberghe | | G06T 11/005 600/436 |
| 2009/0250616 A1* | 10/2009 | Solf | | G01T 1/2985 250/363.04 |
| 2010/0074500 A1* | 3/2010 | Defrise | | G06T 11/006 382/131 |
| 2016/0216385 A1* | 7/2016 | Moskal | | G01T 1/2985 |

* cited by examiner

METHOD FOR RECONSTRUCTING MULTI-TRACER METABOLIC AND MORPHOMETRIC IMAGES AND TOMOGRAPHY SYSTEM FOR MULTI-TRACER METABOLIC AND MORPHOMETRIC IMAGING

TECHNICAL FIELD

This application relates to the field of time-of-flight positron emission tomography (TOF-PET), and a method of imaging using data acquired by a TOF-PET scanner, and particularly to fast event-by-event analytical reconstruction method and system for use in creation of simultaneous multi-tracer morphometric images in PET.

BACKGROUND OF THE INVENTION AND CROSS REFERENCE TO RELATED APPLICATIONS

The positron emission tomography (PET) is a branch of nuclear medicine in which the selected radiopharmaceutical is introduced into the body of a patient. PET radiopharmaceuticals comprise radioactive isotopes as e.g. $^{18}F$ or $^{11}C$ which undergo beta-plus decay and emits a positron (anti-electron). The emitted positron penetrates the object's tissues, where it annihilates with electron from a tissue component. Thereby, the mass of both particles is converted into two or more gamma quanta.

The current PET tomography scanners use annihilation into two gamma quanta having energy of 511 keV and emitted into opposite directions in the electron-positron pair's rest frame. This straight line of gamma quanta emission is referred to as line of response (LOR) and it is reconstructed for each registered event. Current TOF-PET scanners additionally utilize information about time difference between the time-of-flights (TOF) of gamma quanta from the annihilation point to the detectors.

Most of the presently available TOF-PET scanners are capable of registration of the 511 keV gamma quanta by means of inorganic crystal scintillators usually arranged in the form of ring surrounding the diagnosed patient. There are also known TOF-PET solutions (e.g. as disclosed by patent applications WO2011008119 and WO2011008118) in which the gamma quanta are registered using organic plastic scintillators. Events corresponding to the registration of two 511 keV gamma quanta are identified based on the energy deposited in scintillators via photoelectric or Compton effects.

The TOF-PET detectors equipped with dedicated electronics and software enable a reconstruction of positions and times of gamma quanta interaction in scintillator material. This information is then further processed by the appropriate software procedures to reconstruct LOR and TOF for each registered event and next plurality of events are used to determine a metabolic image of the density distribution of radiopharmaceuticals in the patient's body.

Radiopharmaceuticals can in general be divided into two classes distinguished by physical properties of applied isotopes. The first class includes isotopes emitting positrons without subsequent emission of prompt gamma quantum as e.g. $^{18}F$ which upon emission of positron changes into ground state of $^{18}O$. The second class comprises isotopes as e.g. $^{44}Sc$ or $^{14}O$ which after emission of positron change into a daughter nucleus in an excited state. The daughter nucleus subsequently de-excites through emission of one or several gamma quanta.

In the current TOF-PET imaging the de-excitation gamma quantum (often referred to as prompt gamma) constitute a source of background since it may give a signal in the detector which can be misclassified as signal from the 511 keV quantum from the electron-positron annihilation. Analogously positron-electron annihilation to the three gamma quanta constitutes a source of unwanted background.

On the other hand the emission of prompt gamma quantum by some of the radio-isotopes may allow for the simultaneous multi-isotope imaging as described e.g. in the patent application WO2012135725. In this application a simultaneous PET imaging with two isotopes one with prompt gamma and one without prompt gamma is disclosed.

Another solutions taking advantage of the registration of the three gamma quanta—two from the positron-electron annihilation and one prompt gamma from the de-excitation of the daughter nucleus—are described e.g. in articles: C. Gringon et al., "Nuclear medical imaging using beta+ gamma coincidences from 44Sc radio-nuclide with liquid xenon as detection medium", *Nucl. Instr. Meth. in Phys. Res. A* 571 (2007) 142, and P. G. Thirolf, C. Lang, K. Parodi, "*Perspectives for Highly-Sensitive PET-Based Medical Imaging Using beta+gamma Coincidences*", *Acta Physica Polonica A* 127 (2015) 1441. These articles present different methods for registration of the direction and energy of the prompt gamma after Compton scattering in the detector material. This additional information combined with the information from the standard TOF-PET detectors (such as times and positions of the interaction of two gamma quanta from the positron-electron annihilation) results in the improvement of the spatial resolution of the reconstruction of the annihilation point.

Recently it was disclosed a method applicable for determining morphometric images of the living organisms based on positron-electron annihilation into both: two and three gamma quanta and utilising a prompt gamma emitted from the daughter nucleus of the isotope used in the radiopharmaceutical.

This new method of imaging involving registration of three or more annihilation gamma quanta is described in patent application WO2015028604 which discloses procedures of morphometric imaging based on the measurement of the life-time of ortho-positronium.

Orthopositronium (o-Ps) atoms are produced inside cells during the PET imaging. Such atoms, being a bound state of positron and electron may be produced and trapped in the free volumes between molecules. The probability of creation and lifetime of ortho-positronium depends strongly on the size of the free volume and thus it is connected to the morphology of the cells and may be used as an indicator of the stage of development of metabolic disorders. Such correlations have been reported e.g. in article by R. Pietrzak et al., "Influence of neoplastic therapy on the investigated blood using positron annihilation lifetime spectroscopy", NUKLEONIKA 2013, 58 (1): pp. 199-202.

In vacuum ortho-positronium atom decays predominantly into three gamma quanta, however inside the diagnosed patient it may also disintegrate via emission of two gamma quanta e.g. due to the pick-off process. Therefore, as described in patent application WO2015028604, in order to determine the ortho-positronium life-time image, for each recorded event, a prompt de-excitation gamma is registered in order to determine a time of creation of the positronium atom, and in addition two or three annihilation gamma quanta are registered in order to determine a time of the decay of this atom. An average ortho-positronium annihilation lifetime ($\tau_{o-Ps}$) and probability of its production ($P_{o-Ps}$) determined for each voxel of the image serves as morphological indicators, additional to and independent of the SUV index (Standardised Uptake Value), which in the standard PET imaging expresses the normalized value of the uptake of the radiopharmaceutical in a given voxel of the organism. Combination of indicators SUV, $\tau_{o-Ps}$, and $P_{o-Ps}$ is more sensitive to the occurrence of metabolic abnormalities in cells. Therefore, images of the positronium life-time and its creation probability (performed simultaneously with the standard PET images) are very helpful in the medical diagnosis.

In the disclosed patent application WO2015028604 a reconstruction of place and time of positron-electron annihilation into three gamma quanta is performed in following steps:

the imaged space of the object is discretized into voxels, and next only these voxels are selected which are in the plane defined by points of interaction of annihilation gamma quanta in the detectors, and further on a $\chi^2(v_a, t_a)$ statistics is defined as a function of annihilation voxel $v_a$ and annihilation time $t_a$ and the place and time of annihilation is chosen as this for which $\chi^2(v_a, t_a)$ reaches a minimum of $\chi^2(v_a, t_a)$, whereby the minimisation is performed over two-dimensional parameters space ($v_a, t_a$).

The above described, known in the state-of-the-art procedure, is used as a step for the ortho-positronium image reconstruction and requires a large and variable number of computation operations while searching for the minimum of the $\chi^2$ function over a space typically of about ($10^4$ voxels)×(3 ns interval).

Therefore, it would be desirable to develop a method allowing for analytical reconstruction of a place of ortho-positronium annihilation into three gamma quanta, which would significantly speed up a reconstruction process, and as a consequence would decrease time needed for the diagnosis of the patient.

It would be also desirable to develop a method enabling determination of the position of ortho-positronium annihilation into three gamma quanta without the necessity of a prior discretization of the image, thus enabling to improve a spatial and temporal resolution of the $\tau_{o-Ps}$ and $P_{o-Ps}$ morphometric images, and hence improving a quality of diagnosis based on the morphometric imaging.

Moreover, it would be advantageous to develop a method and a device which would allow for multi-tracer imaging, preferably with more than two tracers, thus decreasing significantly the time needed for the sequential imaging which need to be long between subsequent scans because of the long (many hours) biological decay time needed for cleaning up a tracer from the organism. Therefore, imaging with more than two tracers in one day is currently impractical though it could enhance significantly the diagnostic possibilities and would be also of great importance for disentangling regions of production of various beta+ isotopes during hadron-therapy.

It is therefore an object of the present invention to provide a new method for reconstructing the time and place of a positron-electron annihilation into three gamma quanta that reduces significantly a number of calculations to perform with respect to the prior art, and that does not worsen the time and position resolution beyond the instrumental limits of TOF-PET scanners, and to provide a device that applying a said method will permit a simultaneous multi-tracer PET and morphometric imaging with unlimited number of distinct tracers emitting prompt gamma quanta.

SUMMARY

There is disclosed a method for reconstructing multi-tracer metabolic and morphometric images by determining time and three-dimensional spatial coordinates of position of positron-electron annihilation into three gamma quanta, the method comprising the steps of:

a) receiving a plurality of events from positron annihilation centers obtained during measurements conducted by TOF-PET tomography, b) reconstructing time and spatial coordinates for plurality of events collected in a), c) determination of a common plane for gamma quanta originating from positron-electron annihilation, d) transforming a time and spatial coordinates for gamma quanta to the decay plane determined in c), e) determining the time and spatial coordinates of the annihilation place in the plane defined in c), f) transforming time and spatial coordinates for an reconstructed annihilation place from decay plane reference frame to the image reference frame.

Preferably the method further comprises determining the common origin point of all three photons in decay plane reference frame by solving the equation system:

$$c^2(T_i-t)^2=(X_i-x)^2+(Y_i-y)^2, i=1,2,3. \quad \text{(Formula 1)}$$

where:

(x,y) are the assumed spatial coordinates of o-Ps decay, t is the assumed time of o-Ps decay, $T_i$ is the recorded time of the gamma quantum hit, $Y_i$ are the spatial coordinates of i-th gamma quantum hit in the detector expressed in decay plane frame of reference, c is the speed of light.

There is also disclosed a tomography system for multi-tracer metabolic and morphometric imaging of an interior of an examined object, wherein, the tomography system includes:

plurality of the TOF-PET detection modules, data acquisition subsystem and data selection subsystem, configured to register and identify all kinds of gamma quanta emitted from the examined object administered with a PET radio-tracer, and a data processing system configured to reconstruct and visualize metabolic and morphometric images for each radio-tracer separately.

Preferably said data processing system is coupled with a memory unit, the memory unit having stored therein sequences of instructions, which, when executed by said data processing system, caused said data processing system to perform the steps of:

i. determination of a common plane for collected gamma quanta from annihilation point, ii. transforming a coordinates of collected gamma quanta from annihilation point from detector reference frame to decay plane reference frame, iii. determining the common origin point of all the photons by solving the equation system given by Formula 1, iv. transforming time and spatial coordinates for an reconstructed annihilation place from decay plane reference frame to the image reference frame.

BRIEF DESCRIPTION OF FIGURES

Example embodiments of present invention are presented on a drawing wherein.

DETAILED DESCRIPTION OF THE INVENTION

For registration of gamma quanta by the presented means, organic scintillator based TOF-PET as well as TOF-PET/MRI and TOF-PET/CT detectors described in patent applications WO2011008119, WO2011008118, WO2015028603 and WO2015028598 can be used, and also standard TOF-PET scanners based on inorganic crystal may be used after appropriate (disclosed in this patent application) modifications in the electronics and data processing algorithms which would enable simultaneous registration and reconstruction of events corresponding to prompt gamma emission and annihilations into 3γ or 2γ.

Figure 1:
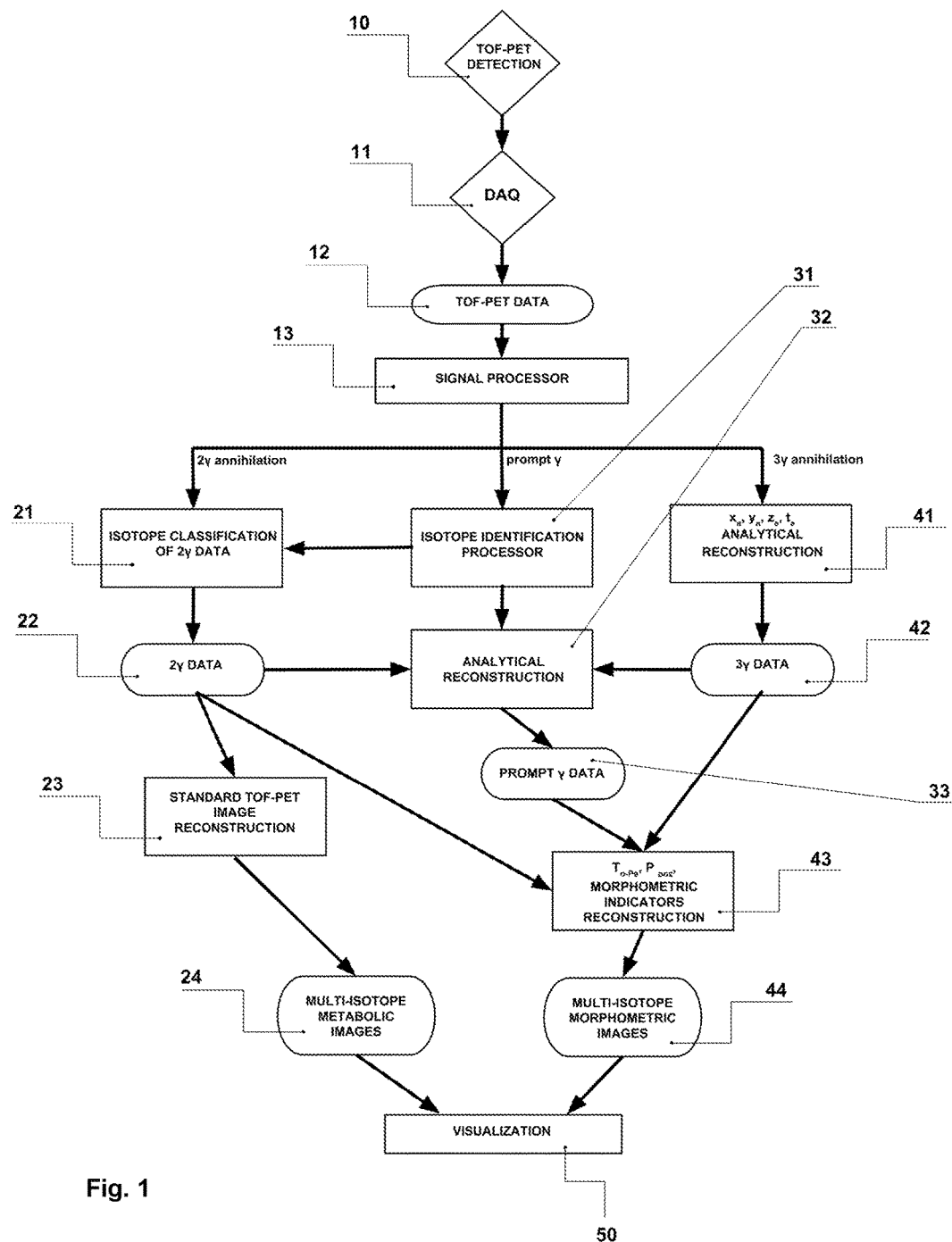
FIG. 1 is a block diagram of the device and process for simultaneous recording of the data and for reconstructing the multi-tracer PET and morphometric images.

FIG. 1 is a block diagram of the device and process for simultaneous recording of the data and for reconstructing the multi-tracer PET and morphometric images. A said device includes a plurality of detectors capable of determining position and time of interaction of gamma quanta emitted from the interior of the examined object. Detectors known in the art (e.g. WO2011008119, WO2011008118, WO2015028603, WO2015028598) may be used for this purpose. Characteristics of signals created in the detectors 10 by the gamma quanta are digitized and collected in step 11 by the data acquisition system (DAQ) and send in step 12 to the processor which processes them further in step 13 or saves them on the disk. Data acquisition may proceed in a standard trigger mode or in a trigger-less mode as described e.g. in the patent application WO2015028594. Characteristics of collected signals are used by the processor 13 to identify signals from prompt gamma, as well as 3γ and 2γ annihilations using methods known to persons skilled in the art, as described e.g. in the patent application WO2015028604. Further on, signals from prompt gamma are analysed by the processor 31 which identifies the tracer, whereby identification is performed e.g. based on the energy deposited in the detectors 10, since the energy of prompt gamma is characteristic for each isotope. The tracer tag is used by processor 21 to group the 2γ data according to the tracer. Next the data 22 are used to reconstruct metabolic images 24 for each tracer using in step 23 methods of TOF-PET known in the state-of-the-art.

Figure 3:
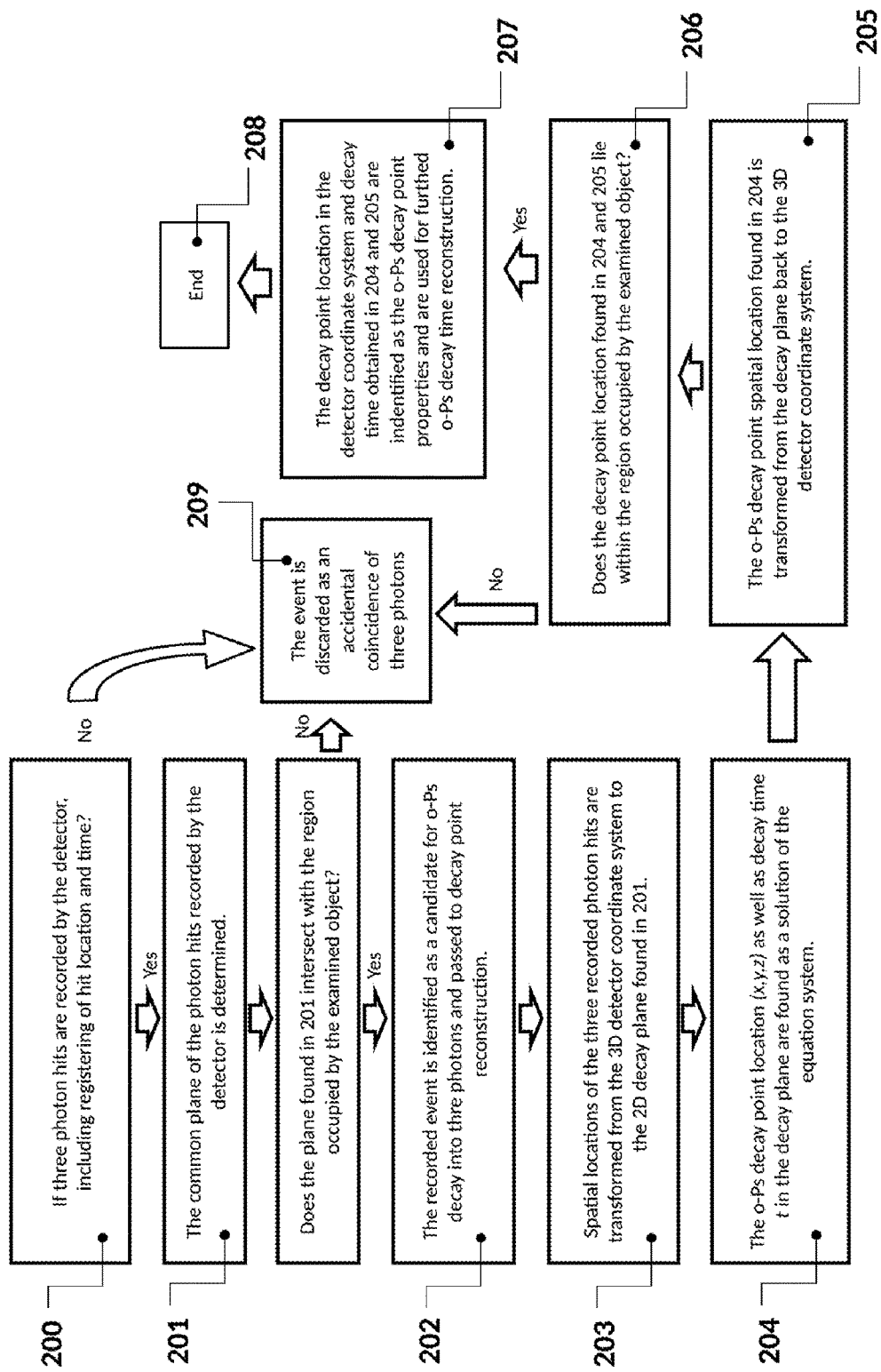
FIG. 3 is an algorithm flow diagram according to the present invention.

The signals from annihilation into 3γ are processed in the step 41 using fast analytical algorithm being a subject of this invention with the flow diagram shown in FIG. 3. Time and position of the annihilation calculated in step 41 are stored in 42 and are further used in step 32 to reconstruct a time of emission of the prompt gamma quanta e.g. using methods disclosed in patent application WO2015028604. Finally 2γ, 3γ, and prompt gamma data in the format stored in 22, 33 and 42 are used in step 43 to reconstruct morphometric indicators $\tau_{o-Ps}$, $P_{o-Ps}$ for each tracer administered to the patient. The reconstructed metabolic 24 and morphometric 44 images can be visualized in step 50.

In order to enhance diagnostic capabilities, the obtained metabolic images 24 may be improved (e.g. corrected for the attenuation of the gamma quanta in the examined object) using anatomical CT or morphological MRI images, whereby these can be determined simultaneously or sequentially by the known in the art CT and MRI tomography methods. Finally the determined metabolic and morphometric image may be superimposed over the CT or MRI images in order to enhance the quality of the diagnosis.

Figure 2:
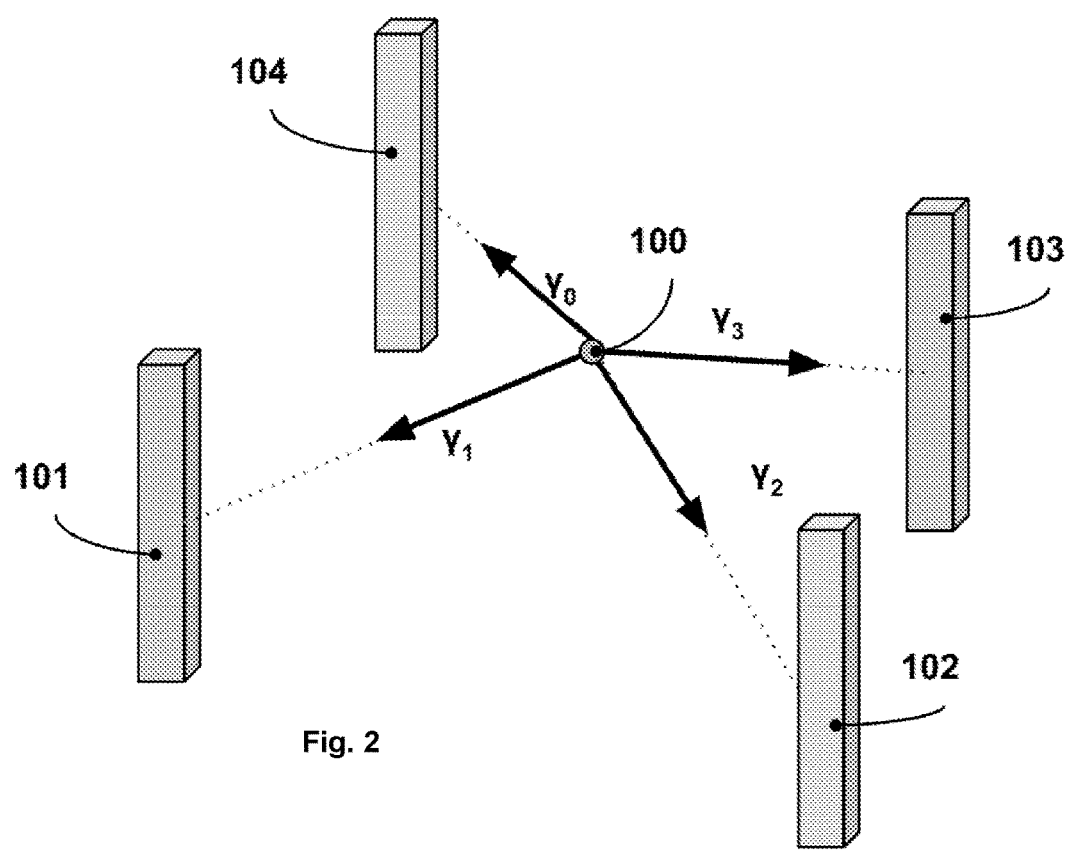
FIG. 2 is a scheme presenting a single event occurring in the interior of the examined object located inside a diagnostic chamber of the TOF-PET scanner.

FIG. 2 shows a single event occurring in the interior of the examined object located inside a diagnostic chamber of the TOF-PET scanner. A prompt gamma quantum ($\gamma_0$) is registered in one of the TOF-PET detector modules 104, while remaining three gamma quanta ($\gamma_1,\gamma_2,\gamma_3$) from the decay of the ortho-positronium atom are registered in other TOF-PET detector components 101,102,103. For each hit, in step 13 from FIG. 1, the spatial location of the point where the gamma quantum interacted with the detecting material is recorded and expressed as three Cartesian coordinates in the frame of reference of the detector. In addition to spatial coordinates of the hits, the time of interaction is recorded for each gamma quantum.

FIG. 3 is an algorithm flow diagram according to the present invention. At step 200 three gamma quantum hits are recorded within a predefined time and energy windows. They are considered a candidate event for the ortho-positronium decay into three gamma quanta taking place in the volume of the examined object.

At step 201 the locations of the gamma quanta hits comprising the candidate event are used to geometrically determine their common plane, further on referred to as the decay plane or plane-of-response (POR). This plane should comprise a place of ortho-positronium annihilation due to the energy and momentum conservation which implies that the momentum vectors of three gamma quanta from the ortho-positronium decay must be co-planar.

The background for decays of ortho-positronium is constituted mostly by random coincidences of gamma quanta originating from direct e+e- and para-positronim annihilations into two gamma quanta with a third accidental gamma quantum from another event, as well as scattered coincidences due to events where one or more of the gamma quantum has undergone Compton scattering in the examined object or in the detector. In order to suppress such background events, the decay plane obtained in step 201 is geometrically checked for intersecting with the volume of the examined object. Events where the gamma quanta were subject to Compton scattering can then be partially rejected 209 if their decay plane is separated from the examined volume.

In step 202 the event candidates that passed this test are then subject to reconstruction of the ortho-positronium decay point and time.

In step 203 the three-dimensional spatial coordinates of three gamma quantum hits are transformed to the two-dimensional frame of reference of the decay plane using a projection onto this plane. The reconstruction of ortho-positronium decay is then reduced to a two-dimensional problem.

Figure 4:
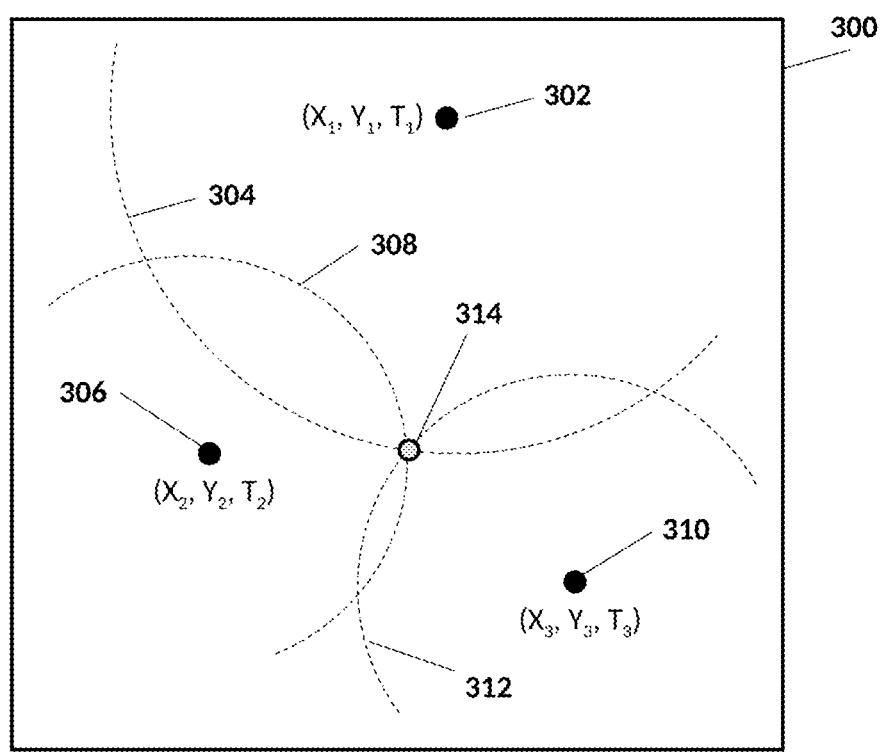
FIG. 4 is a scheme presenting the idea of reconstruction of the ortho-positronium decay point in the reference frame related to the decay plane.

FIG. 4 depicts the idea of reconstruction of the ortho-positronium decay point 314 in the reference frame related to the decay plane 300.

In step 204 for an i-th gamma quantum hit (where i=1,2,3) 302, 306, 310, and if the ortho-positronium decay is assumed to take place at time t, the set of possible origin points of the associated gamma quanta is represented by a circle 304, 308 and 312 respectively for 302, 306 and 310 centered at the hit location in the detector and with a radius of $c(T_i-t)$ where $T_i$ is the recorded time of the gamma quantum hit and c is the speed of light. Definition of such set of possible origin points for each of the photons leads to the following system of equations:

$$c^2(T_i-t)^2=(X_i-x)^2+(Y_i-y)^2, i=1,2,3. \quad \text{(Formula 1)}$$

Since the o-Ps→3γ decay point is the common origin point of all three gamma quanta, it is found as the intersection of the circles 314 i.e. by solving the equation system (Formula 1). An closed-form analytical solution of this system is possible and yields simultaneously the location (x,y) of the decay point in the decay plane and the decay time t.

In step 205 in order to obtain the three-dimensional decay location in the reference frame of the detector, a geometrical transformation reverse to the one used in 203 is applied to the decay point location expressed in the decay plane.

In step 206 a background rejection is then performed by checking if the decay point obtained in step 205 lies within the volume of the examined object. This allows for partial rejection of background events from random coincidences between annihilation into two photons and a third accidental one. If the decay point lies outside of the examined volume, the event is discarded 209. The shape of the examined object may be obtained from the metabolic image 24 (in FIG. 1), or from CT or MRI images performed prior to the TOF-PET examination.

The reconstruction method described herein does not rely on any assumptions about the discretization of the examined object volume, such as voxelization. Therefore, it is capable of reconstructing the decay point and time with an accuracy limited only by the resolution of the device employed to detection of the gamma quanta hits. Conversely, the techniques known in the present state of the art WO2015028604 divide the examined volume into voxels already at the reconstruction stage and reconstruct the decay point with an accuracy of the size of a single voxel, which introduces an artificial limit on both spatial and time resolution of the o-Ps→3γ decay. The method presented herein is free of this resolution limit. Even though the voxelization must eventually be applied for the need of ortho-positronium lifetime imaging, the lack of discretization of the examined object at the reconstruction level results in a more accurate reconstruction of decay times which enter the o-Ps lifetime determination.

Moreover, the reconstruction presented herein obtains the location and time of the ortho-positronium decay using an analytical recipe based on geometrical considerations, which is performed in a constant computational time, i.e. using always a constant number of arithmetic operations. Meanwhile, the present state of the art techniques use an iterative multi-dimensional optimization technique WO2015028604 which requires repetitive computations with quality of the result being dependent on the number of repetitions. Therefore, the reconstruction method used in this invention significantly reduces the computational load on the device used for reconstruction.

In addition the invented method and system based on TOF-PET detectors capable of registration of signals from 2γ annihilation, 3γ annihilation and prompt gamma, and capable of identifying prompt gamma, allows for tagging events originating from various isotopes. This information enables to classify registered events according to radio-tracer, and hence enabling diagnosis with two or more tracers simultaneously during single PET examination and enabling disentangling regions of production of various beta+ isotopes during hadron-therapy.

The invention claimed is:

1. A method for reconstructing multi-tracer metabolic and morphometric images by determining time coordinates and three-dimensional spatial coordinates of a position of a positron-electron annihilation into three gamma quanta, the method comprising the steps of:
   a) receiving a plurality of events from positron annihilation centers obtained during measurements conducted by TOF-PET tomography;
   b) reconstructing the time coordinates and the three-dimensional spatial coordinates for the plurality of events collected in step (a);
   c) determining a common decay plane for gamma quanta originating from the positron-electron annihilation;
   d) transforming the three-dimensional spatial coordinates for the gamma quanta to a two-dimensional frame of reference of the common decay plane determined in step (c);
   e) determining the time coordinates and the spatial coordinates of a place of the annihilation in the common decay plane defined in step (c);
   f) transforming time coordinates and the spatial coordinates of the place of the annihilation in the two-dimensional frame of reference of the common decay plane to three-dimensional spatial coordinates in a detector coordinate system.

2. The method of claim 1, further comprising determining a common origin point of all photons in the reference frame of the common decay plane by solving an equation system:

$$c^2(T_i-t)^2=(X_i-x)^2+(Y_i-y)^2, i=1,2,3 \quad \text{(Formula 1)}$$

wherein:
   (x,y) are the assumed spatial coordinates of the o-Ps decay point in the two-dimensional frame of reference of the common decay plane,
   t is the assumed time of the o-Ps decay,
   $T_i$, is a received time coordinate of the gamma quantum hit,
   $X_i$, $Y_i$ are the spatial coordinates of the i-th gamma quantum hit in the two-dimensional frame of reference of the common decay plane,
   c is the speed of light.

3. A tomography system for multi-tracer metabolic and morphometric imaging of an interior of an examined object, wherein the tomography system includes:
   a plurality of TOF-PET detection modules;
   a data acquisition subsystem;
   a data selection subsystem configured to register and identify all kinds of gamma quanta emitted from an examined object administered with a PET radio-tracer; and
   a data processing system configured to reconstruct and visualize multi-tracer metabolic and morphometric images for each radio-tracer separately by:
      a) receiving from the data acquisition system a plurality of events from positron annihilation centers obtained during measurements conducted by the TOF-PET detection modules;
      b) reconstructing the time coordinates and the three-dimensional spatial coordinates for the plurality of events collected in step (a);
      c) determining a common decay plane for gamma quanta originating from the positron-electron annihilation;

d) transforming the three-dimensional spatial coordinates for the gamma quanta to a two-dimensional frame of reference of the common decay plane determined in step (c);
e) determining the time coordinates and the spatial coordinates of a place of the annihilation in the common decay plane defined in step (c);
f) transforming the time coordinates and the spatial coordinates of the place of the annihilation in the two-dimensional frame of reference of the common decay plane to three-dimensional spatial coordinates in a detector coordinate system.

\* \* \* \* \*